(12) United States Patent
McVey et al.

(10) Patent No.: US 7,629,500 B2
(45) Date of Patent: *Dec. 8, 2009

(54) ACTIVATED VAPOR TREATMENT FOR NEUTRALIZING WARFARE AGENTS

(75) Inventors: Iain F. McVey, Lakewood, OH (US); Lewis I. Schwartz, Shaker Heights, OH (US); Michael A. Centanni, Parma, OH (US); George W. Wagner, Elkton, MD (US)

(73) Assignees: Steris Inc, Temecula, CA (US); The United States of America as represented by the Secretary of the Army, Washington, DC (US)

( * ) Notice: Subject to any disclaimer, the term of this patent is extended or adjusted under 35 U.S.C. 154(b) by 610 days.

This patent is subject to a terminal disclaimer.

(21) Appl. No.: 10/554,223

(22) PCT Filed: Apr. 23, 2004

(86) PCT No.: PCT/US2004/012744

§ 371 (c)(1),
(2), (4) Date: Oct. 20, 2005

(87) PCT Pub. No.: WO2005/035067

PCT Pub. Date: Apr. 21, 2005

(65) Prior Publication Data

US 2006/0205991 A1    Sep. 14, 2006

(51) Int. Cl.
*A62D 101/02* (2007.01)
*A62D 3/35* (2007.01)
*A62D 3/38* (2007.01)
*A62D 101/26* (2007.01)
*A62D 101/28* (2007.01)

(52) U.S. Cl. .............. 588/300; 588/401; 588/408; 588/409; 588/317; 588/320; 588/299

(58) Field of Classification Search ............... 588/299, 588/312, 317, 320, 401, 408, 409
See application file for complete search history.

(56) References Cited

U.S. PATENT DOCUMENTS 4,042,336 A    8/1977    Larsson (Continued)

FOREIGN PATENT DOCUMENTS

DE    300 472 A7    6/1992

(Continued)

OTHER PUBLICATIONS

U.S. Appl. No. 10/422,474, filed Apr. 2003, McVey et al.*

(Continued)

*Primary Examiner*—Timothy C Vanoy
*Assistant Examiner*—Daniel Berns
(74) *Attorney, Agent, or Firm*—Fay Sharpe LLP

(57) ABSTRACT

Hydrogen peroxide is vaporized (20) and mixed (30) with ammonia gas in a ratio between 1:1 and 1:0.0001. The peroxide and ammonia vapor mixture are conveyed to a treatment area (10) to neutralize V-type, H-type, or G-type chemical agents, pathogens, biotoxins, spores, prions, and the lip-,e. The ammonia provides the primary deactivating agent for G-type agents with the peroxide acting as an accelerator. The peroxide acts as the primary agent for deactivating V-type and H-type agents, pathogens, biotoxins, spores, and prions. The ammonia acts as an accelerator in at least some of these peroxide deactivation reactions.

40 Claims, 7 Drawing Sheets

U.S. PATENT DOCUMENTS

| | | | |
|---|---|---|---|
| 4,695,327 A | 9/1987 | Grebinski | |
| 4,867,799 A | 9/1989 | Grebinski | 134/11 |
| 4,896,547 A | 1/1990 | Arney et al. | |
| 5,430,228 A | 7/1995 | Ciambrone et al. | 588/200 |
| 5,667,753 A | 9/1997 | Jacobs et al. | |
| 5,714,128 A | 2/1998 | Ritter | 422/211 |
| 5,779,973 A | 7/1998 | Edwards et al. | |
| 5,998,691 A * | 12/1999 | Abel et al. | 588/318 |
| 6,011,193 A | 1/2000 | Myler et al. | |
| 6,080,906 A | 6/2000 | Johnson et al. | |
| 6,096,283 A | 8/2000 | Cooper et al. | |
| 6,121,506 A | 9/2000 | Abel et al. | |
| 6,132,628 A | 10/2000 | Barak | |
| 6,245,957 B1 | 6/2001 | Wagner et al. | 588/200 |
| 6,375,697 B2 | 4/2002 | Davies | |
| 6,566,574 B1 | 5/2003 | Tadros et al. | |
| 6,790,249 B2 | 9/2004 | Davies | |
| 6,855,328 B2 | 2/2005 | Hei et al. | |
| 7,102,052 B2 * | 9/2006 | McVey et al. | 588/303 |
| 2001/0049926 A1 | 12/2001 | Davies | |
| 2003/0035754 A1 | 2/2003 | Sias et al. | |
| 2003/0045767 A1 | 3/2003 | Brown | 588/200 |

FOREIGN PATENT DOCUMENTS

| | | |
|---|---|---|
| DE | 326 735 | 6/1992 |
| DE | 19732594 | 2/1999 |
| EP | 1 166 825 A1 | 1/2002 |
| EP | 1 291 040 A2 | 3/2003 |
| FR | 2651133 | 3/1991 |
| FR | 2766724 | 2/1999 |
| JP | 2002066308 | 3/2002 |
| SU | 1681860 A1 * | 10/1991 |
| WO | WO 03/090875 A1 | 11/2003 |

OTHER PUBLICATIONS

U.S. Appl. No. 11/401,649, filed Apr. 11, 2006, McVey et al.

Wagner, et al., Rapid Nucleophilic/Oxidative Decontamination of Chemical Warfare Agents, *Ind. Eng. Chem. Res.*, 2002, 41, 1925-1928.

\* cited by examiner

ACTIVATED VAPOR TREATMENT FOR NEUTRALIZING WARFARE AGENTS

GOVERNMENT INTEREST

The invention described herein may be manufactured, licensed, and used by or for the U.S. government.

BACKGROUND OF THE INVENTION

The present application relates to the art of deactivating biological and chemical warfare agents. It finds particular application in conjunction with G-type, V-type, and H-type nerve agents, as well as biological agents.

Chemical warfare agents include G-type, V-type, and H-type agents. G-type agents are phosphor containing and are clear, colorless, and tasteless liquids that are miscible in water and most organic solvents. Examples include ethyl-N,N dimethyl phosphoramino cyanidate (Tabun or agent GA), phosphonofluoridate esters, such as isopropyl methyl phosphonofluoridate (Sarin or Agent GB), and methylphosphonofluoridic acid 1,2,2-trimethylpropyl ester (Soman or Agent GD). GB is odorless and is the most volatile nerve agent, evaporating at about the same rate as water. GA has a slightly fruity odor, and GD has a slight camphor-like odor. H-type agents include di(2-chloroethyl) sulfide (mustard gas or Agent HD) and dichloro (2-chlorovinyl) arsine (Lewisite).

V-type nerve agents contain a substituted amine group, and include methyl phosphonothiolates having an internal amino group. Examples include o-ethyl-S-(2-diisopropyl aminoethyl) methyl phosphono-thiolate (agent VX), O-isobutyl-S-(2-diethyl) ethyl methylphosphonothiolate, and O,S-diethyl methylphosphonothiolate. The phosphonothiolates form toxic hydrolysis products comprising phosphonothioic acids. VX is a clear, amber-colored, odorless, oily liquid. It is miscible with water and soluble in all solvents. It is the least volatile nerve agent.

Liquid oxidants have been developed which can deactivate biological warfare agents. See, for example, U.S. Pat. No. 6,245,957 to Wagner, et al. In Wagner, a strong oxidant solution is sprayed as a liquid onto equipment in the field which is or has potentially been contaminated with biological or chemical warfare agents. After treatment, the solution is rinsed from the equipment with water which can be permitted to flow onto the ground as non-toxic waste. Although effective, the liquid Wagner solution has drawbacks. First, it is difficult for liquids to penetrate crevices, fine cracks, ducts, and partially protected or overlapping parts. Second, in enclosed spaces such as the interior of airplanes, tanks, and buildings, cleanup and disposal of the liquid solution can be problematic. Third, liquids can damage some equipment, such as electronic or electrical equipment.

Blistering agents, such as HD (sulfur mustard) undergo oxidation to non-vesicating products (sulfide to sulfoxide). With the correct choice of agents, the further oxidation to the sulfone does not occur. This is preferable as both the sulfide and the sulfone have vesicant properties; whereas, the sulfoxide is non-vesicant.

Peroxide causes a perhydrolysis reaction neutralizing V-type nerve agents, such as VX nerve agent. In the perhydrolysis reaction, the peroxide moiety substitutes one of the groups around the phosphorous atom at the active site of the nerve agent molecule. Perhydrolysis is more effective against V-type nerve agents than base catalyzed hydrolysis by water. In the presence of water, such as a water and ammonia wash, the base catalyzed hydrolysis reaction can form EA2192 which is also highly toxic. EA2192 is a phosphonothioic acid which has the same basic structure as VX except that the terminal ethoxy group is replaced with OH.

On the other hand, G-agents, such as GD tend to be quite stable in the presence of hydrogen peroxide. GD does not undergo an autocatalytic perhydrolysis neutralizing reaction with hydrogen peroxide. Rather, G-type agents are typically deactivated with liquid hydrogen peroxide by base catalysis. Specifically, ammonia has been used to facilitate the base catalyzed hydrolysis of agents with liquid hydrogen peroxide, or perhydrolysis. Molybdate ions have also been used in combination with liquid hydrogen peroxide. The permolybdate ions formed have been found to deactivate G, V and H-agents.

The present application delivers a vapor phase deactivator which is effective against G, V, and H-type agents, as well as against biological agents.

SUMMARY OF THE INVENTION

In accordance with one aspect of the present invention, a method of deactivating a pathogenic chemical agent is provided. The method includes subjecting the pathogenic chemical agent to a peroxide and a nitrogen containing compound of the general formula:

$$R_1 - N - R_2$$
$$|$$
$$R_3$$

where $R_1$, $R_2$, and $R_3$ independently are selected from H and an alkyl group.

In accordance with another aspect of the present invention, an apparatus for deactivating a pathogenic chemical agent is provided. The apparatus includes a means for subjecting the pathogenic chemical agent to a mixture of a strong oxidant compound and an alkaline compound, both in a gaseous form.

In accordance with another aspect of the present invention, a method for decontamination of an item contaminated with GD. The method includes contacting the item in an enclosure with a vapor containing a peroxide and ammonia for sufficient time to reduce the concentration of GD to less than about 1% of its initial concentration, the time for the concentration to reach 1% of its initial concentration being less than 6 hrs.

In accordance with another aspect of the present invention, a method of deactivating a pathogenic chemical agent is provided. The method includes forming a peroxide vapor, increasing the pH of the vapor with a pH-increasing compound, and, subjecting the pathogenic chemical agent to the peroxide at the increased pH for sufficient time to deactivate the chemical agent.

In accordance with another aspect of the present invention, a method of deactivating a biologically active substance is provided. The method includes subjecting the biologically active substance to a mixture of a strong oxidant compound and an alkaline compound, both in a gaseous form.

In accordance with more limited aspects of the present invention, the surfaces are optionally treated with a combination of an oxidizing vapor and a basic vapor, fog, or mist, preferably ammonia or a short chain alkyl amine.

One advantage of at least one embodiment of the present invention resides in its effectiveness against a wide variety of chemical warfare agents including both V and G-type agents as well as biological warfare agents.

Another advantage of at least one embodiment of the present invention resides in its effectiveness against both chemical and biological warfare agents.

Another advantage of at least one embodiment of the present invention resides in its ease of cleanup.

Yet another advantage of at least one embodiment of the present invention resides in compatibility with electrical equipment.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
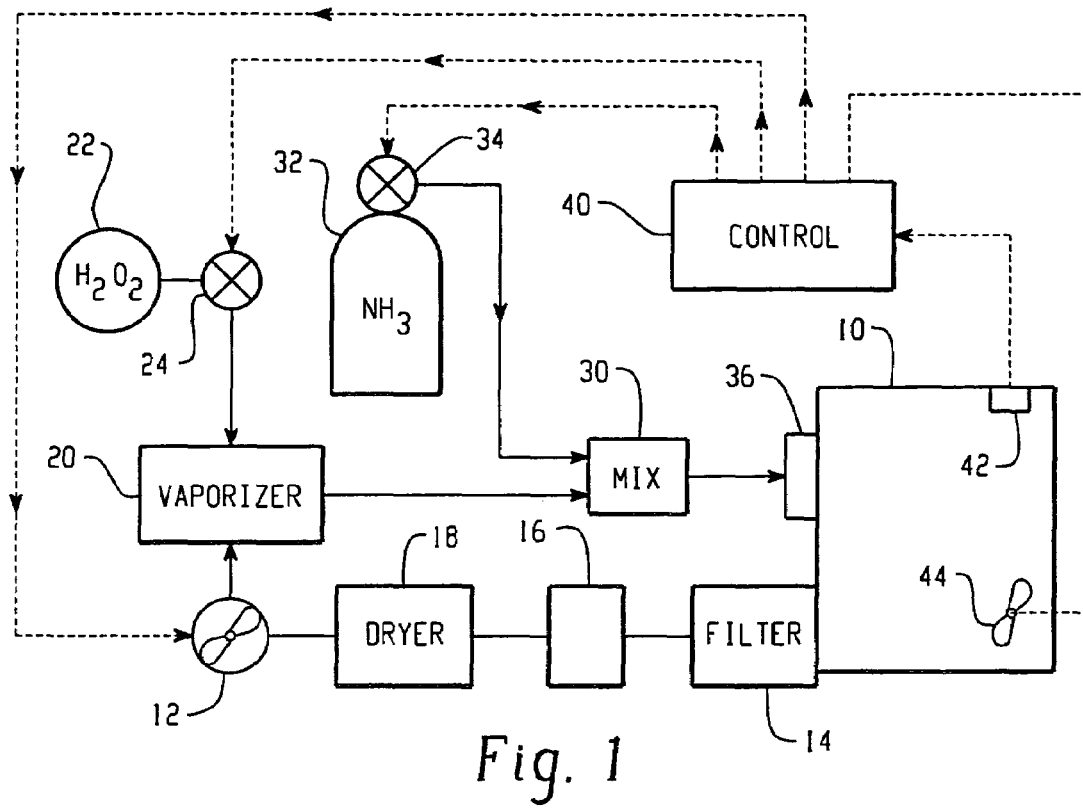
FIG. 1 is a diagrammatic illustration of a vapor treatment system in accordance with the present invention.
Figure 2:
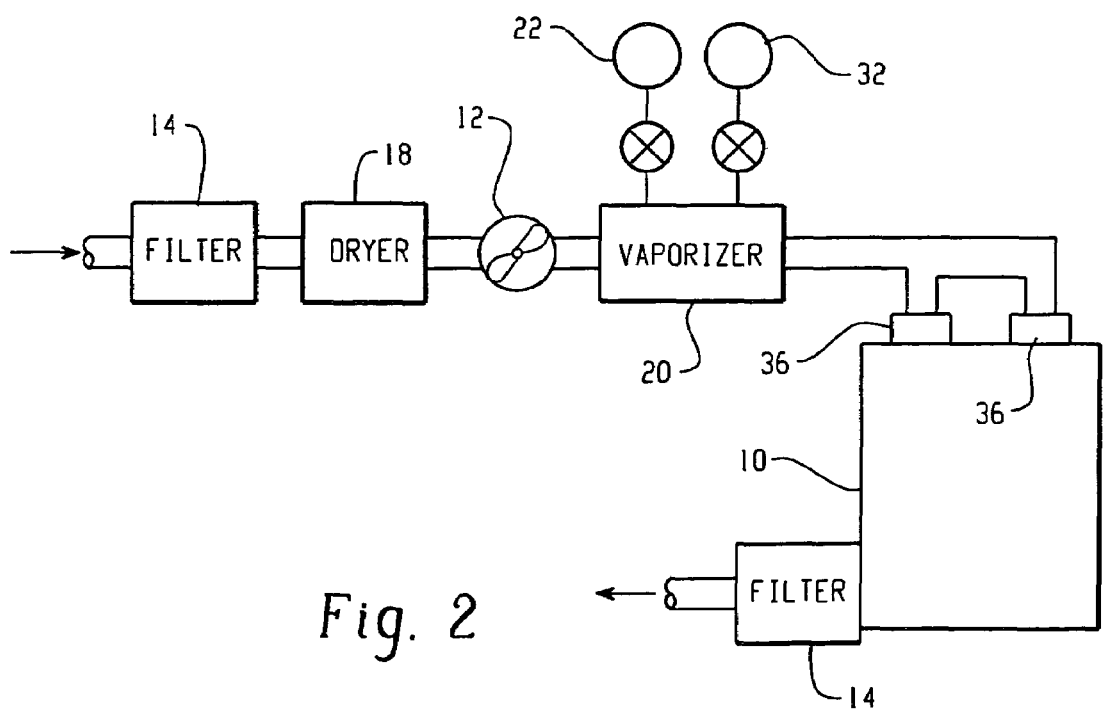
FIG. 2 is an alternate embodiment of the treatment system of FIG. 1.
Figure 3:
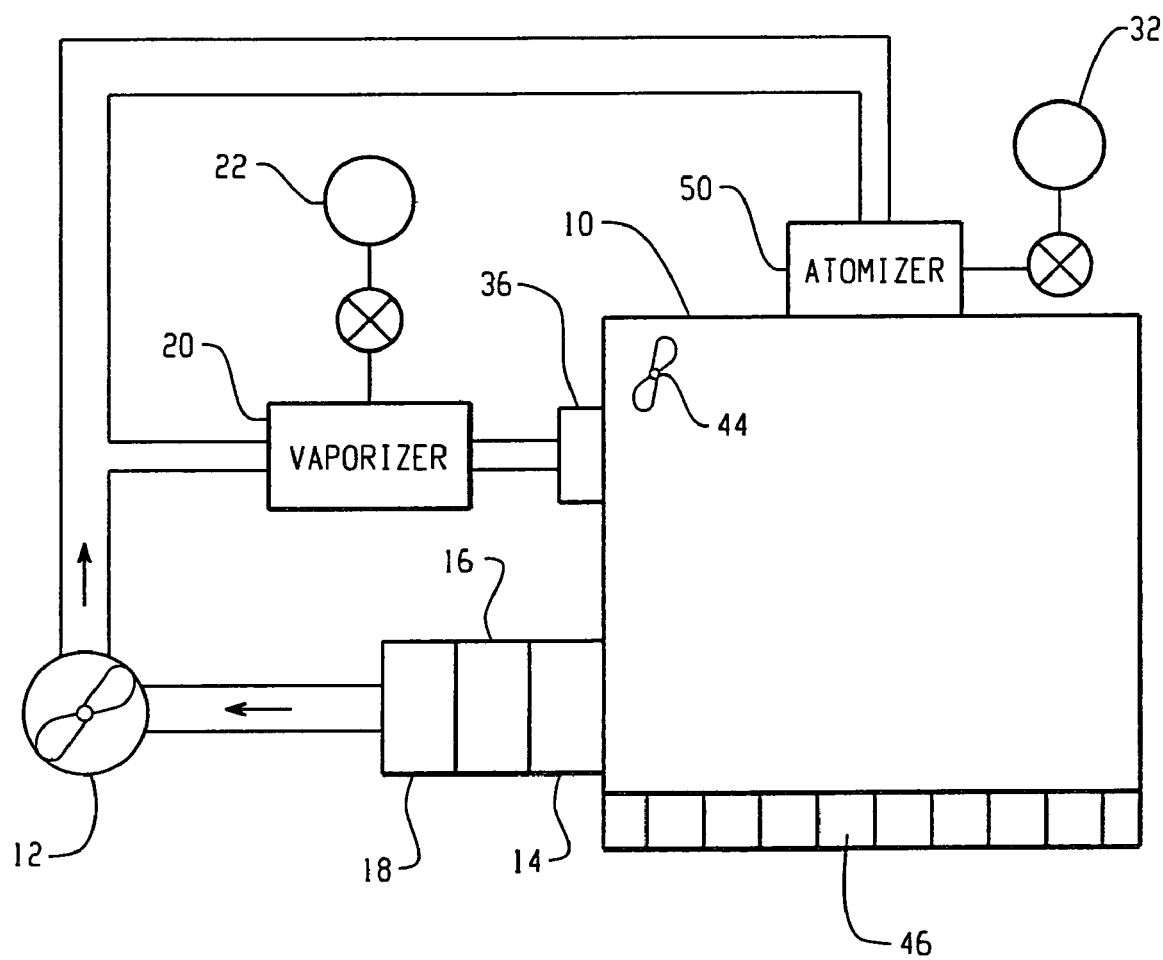
FIG. 3 is another alternate embodiment of the vapor treatment system.
Figure 4:
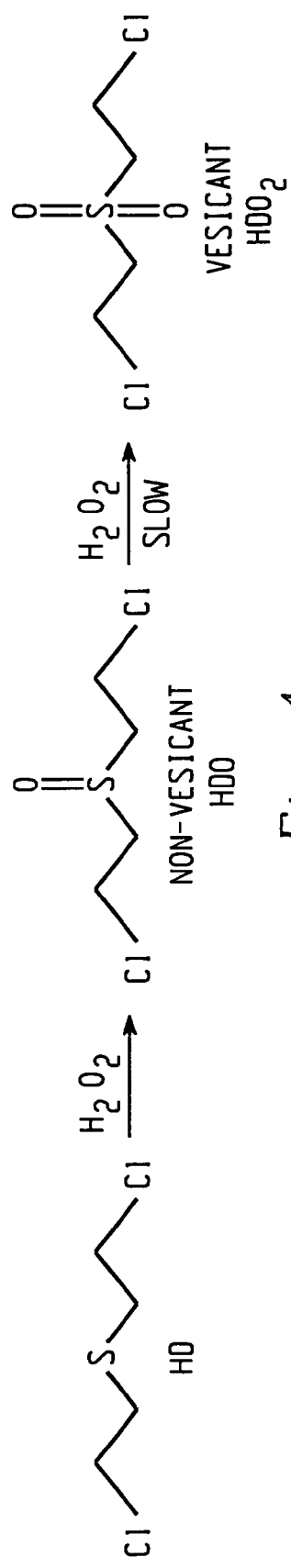
FIG. 4 is a proposed reaction scheme for the conversion of agent HD to reaction products HDO and $HDO_2$ in the presence of hydrogen peroxide.

With reference to FIG. 1, a treatment enclosure 10 receives or is itself a part of a structure potentially contaminated with biologically active substances, particularly biological or chemical warfare agents. Typically, biologically active substances include pathogens, biotoxins, prions, spores, chemical agents, and the like. Typical chemical agents include H-type blistering agents such as mustard gas, and V-type and G-type nerve agents.

The treatment chamber or enclosure 10, in one embodiment, is a dedicated chamber that is adapted to receive items to be generated and then sealed. Items to be decontaminated may include equipment, weapons, clothing, medical instruments, and the like. The chamber can be a fixed structure, a tent that is mounted around the object to be treated, a mobile chamber, or the like. In another embodiment, the enclosure includes the interior of a warehouse, room, aircraft, ship, tank, or other vehicle whose interior surfaces or items contained therein are to be treated.

A fan or blower 12 draws environmental gas, typically air, from the enclosure 10 through a biological or chemical hazard filter 14. A catalytic destroyer 16 breaks down hydrogen peroxide into water vapor. A dryer 18 removes the water vapor from the recirculated gas to control the humidity of the carrier gas.

The filtered and dried air or other carrier gas is supplied to a vaporizer 20 which vaporizes a liquid oxidant, preferably hydrogen peroxide solution, from a liquid hydrogen peroxide source 22. In particular, the vaporizer supplies heat to the liquid oxidant to convert it to vapor form. The heat applied is sufficient to vaporize the hydrogen peroxide and water without leading to premature decomposition of hydrogen peroxide.

While particular reference is made to peroxides, particularly hydrogen peroxide, other strong oxidants such as hypochlorites, ozone solutions, peracids, such as peracetic acid, and the like are also contemplated. Optionally, a cosolvent, such as alcohol, is mixed with the oxidant liquid. A valve 24 or other appropriate control means controls a rate at which the liquid hydrogen peroxide is vaporized.

The hydrogen peroxide vapor is fed to a mixing chamber or region 30 where the hydrogen peroxide vapor and air mixture is mixed with a basic gas, fog, or mist (all of which will be referred to herein as gaseous states, unless otherwise indicated), preferably ammonia gas. However, other nitrogen-containing compounds capable of enhancing the rate of degradation of at least one biologically active substance and/or reducing the concentration of at least one pathogenic product of the degradation of a biologically active substance are also contemplated, such as short chain alkyl amines, e.g., $C_1$-$C_8$ alkyl amines. An exemplary active nitrogen-containing compound can thus be described by the general formula:

$$R_1 - N - R_2 \atop | \atop R_3$$

where $R_1$, $R_2$, and $R_3$ independently are selected from H and an alkyl group. The alkyl group may be substituted or unsubstituted. Suitable substituents are those which do not unduly influence the catalytic activity of the nitrogen-containing compound. The nitrogen containing compound preferably is one which is capable of persisting in the hydrogen peroxide vapor phase or in contact with the biologically active substance for sufficient time to act as an accelerator for the peroxide degradation of the agent. Suitable alkyl amines include methyl amine, ethyl amine, propyl amine, butyl amine, dimethyl amine, methyl ethyl amine, diethyl amine, combinations thereof, and the like.

In the illustrated embodiment, ammonia gas (or other nitrogen-containing compound) is supplied from a source or reservoir 32, such as a high pressure tank holding compressed ammonia gas. A control or regulator valve 34 controls the amount of ammonia vapor supplied to the mixing region 30. The mixture of ammonia and hydrogen peroxide vapor is immediately and continuously supplied to the treatment chamber 10. Optionally, a biological or chemical contaminant filter 36 is mounted at an inlet to the chamber.

In one embodiment, the hydrogen peroxide and ammonia are mixed just prior to or as they enter the enclosure 10. In one specific embodiment, they are fed to the enclosure along separate fluid lines and mix within the enclosure.

A controller 40 is connected with one or more monitors 42 disposed in the treatment chamber 10 for monitoring ambient conditions. Based on the monitored ambient conditions, the controller controls one or more of the control valves 24, 34 to control one or more of the relative concentrations of hydrogen peroxide and ammonia vapor, the blower 12 to control the amount of air flow, fans 44 in the chamber for distributing the treatment gas around the chamber, and the like. Preferably, the controller 40 controls the valves 24, 34 such that a mixture of peroxide vapor and ammonia in the mixing region 30 occurs which achieves an ammonia concentration with a range of 1 to 0.0001 times the nominal peroxide vapor concentration.

In one embodiment, the ammonia concentration in the treatment chamber 10 is at least 1 ppm by weight. The ammonia concentration in the treatment chamber 10 can be up to about 100 ppm, by weight. In one specific embodiment, the ammonia concentration in the treatment chamber 10 is in the range of 3-20 ppm, by weight. In one embodiment, the hydrogen peroxide concentration is at least 50 ppm by weight (0.67 mg/L). The hydrogen peroxide concentration in the treatment chamber 10 can be up to about 3600 ppm, by weight (5 mg/L), or higher. In one specific embodiment, the hydrogen peroxide concentration in the treatment chamber 10 is in the range of 200-1000 ppm, by weight. For example, the ammonia concentration may be about 8 ppm and the hydrogen peroxide, about 600 ppm. To achieve such concentrations in a small enclosure of about 0.1-0.2 $m^3$, a flow rate of about 0.03-0.05 $m^3$/minute hydrogen peroxide vapor and carrier gas is suitable. $NH_3$ gas can be introduced into the VHP stream at about 0.18 mL/min just prior to its entering the enclosure. For larger enclosures, higher flow rates may be appropriate.

In one embodiment, the hydrogen peroxide is replenished intermittently or continuously to maintain a selected concentration range in the enclosure 10. In another embodiment, the enclosure is sealed once the concentration of hydrogen peroxide and/or ammonia has reached a selected level, or at some time thereafter. The concentration is allowed to fall naturally over time due to decomposition. For example, the hydrogen peroxide and ammonia may be fed to the enclosure for an initial period of about four to six hours and then the enclosure sealed, allowing residual amounts of chemical agents and their pathogenic reaction products to be destroyed over a subsequent period of about ten to twenty hours. The vaporizer can be disconnected after the initial period and used to decontaminate another enclosure.

The enclosure 10 can be maintained by a suitable heater 46 (as shown in FIG. 3) at or about room temperature (about 15-30° C.) preferably, about 23-25° C.

In the embodiment of FIG. 1, a closed-loop system is illustrated in which the same carrier gas is recirculated and used over. Alternately, an open-loop system can be utilized, in which fresh atmospheric air is supplied to the vaporizer, preferably filtered and dried, and air exiting the chamber is filtered to prevent the biological or chemical contaminants from escaping and discharging to the atmosphere.

With reference to FIG. 2 an open-loop system is illustrated. The blower 12 pulls air through a filter 14 and, optionally a dehumidifier, before pushing it through the vaporizer 20. A peroxide vapor source 22 and a source 32 of an active nitrogen containing compound provide liquid peroxide and nitrogen containing compound to the vaporizer. Alternately, where the nitrogen containing compound is a liquid, separate vaporizers may be provided for each. The peroxide and nitrogen containing compound can be injected separately into the carrier gas in a mixing region. As yet another alternative, the nitrogen containing compound and the peroxide can be supplied to the vaporizer alternately, as liquids. The output of the vaporizer is connected to an interior region with surfaces to be decontaminated.

With reference to FIG. 3, the carrier gas is filtered 14, peroxide destroyed 16, and dried 18. The blower 12 blows the dry gas to the vaporizer 20 which vaporizes liquid peroxide from the source 22. The peroxide vapor is supplied directly to the treatment region 10. An atomizer 50 receives a liquid alkaline solution from a reservoir 52 which it atomizes or mists into mist that is discharged into the chamber 10. A portion of the carrier gas optionally flows through the mister to entrain and carry the mist throughout the chamber. Alternately, the alkaline solution can be vaporized. Suitable alkaline solutions include water-based solutions of potassium and other carbonates, molybdates, ammonium salts, and the like.

In another embodiment, the hydrogen peroxide vapor and ammonia are introduced sequentially. For example, ammonia is added first. After a time period sufficient for the ammonia to circulate through the enclosure 10, the hydrogen peroxide is allowed to flow into the enclosure.

In another embodiment, at least one of the hydrogen peroxide vapor and ammonia is generated in situ, within the enclosure.

Hydrogen peroxide vapor alone is relatively effective against blistering agents, HD, and nerve agents, such as VX, which exhibit selective oxidation and selective perhydrolysis. By the addition of ammonia to the vapor stream, the hydrolysis-based deactivation of GD is also effected. Improvements in the deactivation rates of blistering agents and nerve agents have also been found.

Without intending to limit the scope of the invention, it is believed that, under exposure to hydrogen peroxide vapor, HD is selectively oxidized to a non-vesicant sulfoxide, HDO (FIG. 4), avoiding formation of the vesicant sulfone ($HDO_2$). This reaction with the vaporized hydrogen peroxide occurs rapidly, more rapidly with vapor than with liquid hydrogen peroxide solutions. A mass transfer of hydrogen peroxide between the vapor and the liquid agent results in an accumulation of hydrogen peroxide in the liquid phase which causes oxidation to occur rapidly. The excess of dissolved oxidant assures completion of the oxidation process.

In liquid neutral peroxide solutions, it is understood that VX undergoes partial autocatalytic perhydrolysis owing to the basicity of its amine group. The VX acts to self-activate peroxide via protonation of the amine group. However, this process may not lead to total destruction. In the presence of activators which buffer the peroxide to basic pHs, the perhydrolysis proceeds to complete destruction.

When exposed to hydrogen peroxide vapor, it is understood that VX undergoes similar perhydrolysis with the basicity of the amine group of the VX molecule effecting autocatalytic perhydrolysis (FIG. 5). A variety of reaction intermediates can be formed, which vary in toxicity, including ethylmethylphosphonate (EMPA) and VX-pyro, a toxic intermediate. However, hydrogen peroxide is constantly replenished by mass transfer between the liquid agent and the vapor flowing over it maintaining an adequate supply of the peroxyl anion for the reaction. The acidic products that are produced by the perhydrolysis are volatile, and are carried away with the flowing vapor. Unlike the stagnant liquids, this removal of the acidic products prevents them from accumulating and lowering the pH to the point that the reaction stops.

The added presence of ammonia has been found to increase the degradation rate of VX by hydrogen peroxide vapor as well as reducing the concentration of toxic byproducts. The reaction is selective for non-toxic EMPA. Little or no EA-2192 forms. VX-pyro tends to be detected only as a non-persistent intermediate. It is suggested that the nitrogen containing compound provides a pH which is more basic than that of hydrogen peroxide alone, thus favoring the reaction pathway to EMPA.

Figure 6:
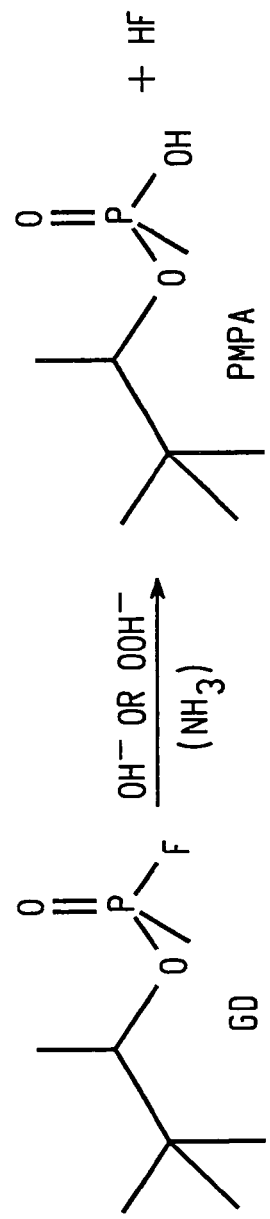
FIG. 6 is a proposed reaction scheme for the conversion of agent GD to PPMA in the presence of hydrogen peroxide and ammonia or an amine.
Figure 5:
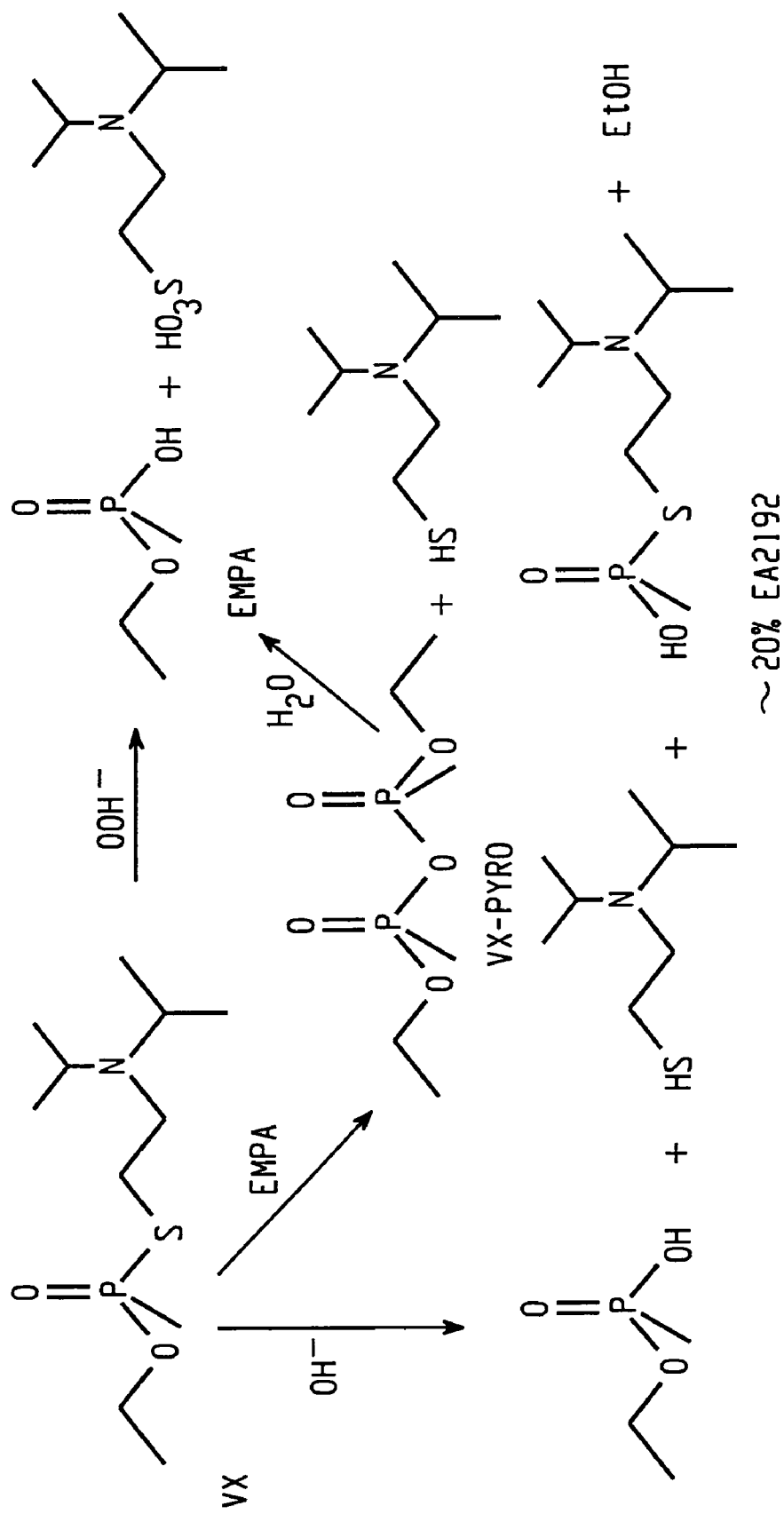
FIG. 5 is a proposed reaction scheme for the conversion of agent VX to VX-Pyro, EMPA and other reaction products in the presence of hydrogen peroxide.

GD does not tend to undergo significant autocatalytic perhydrolysis with either liquid or vaporized hydrogen peroxide alone. However, the GD is susceptible to deactivation by base catalyzed hydrolysis and perhydrolysis. In solution, perhydrolysis is about four times as fast as base catalyzed hydrolysis. Both hydrolysis and perhydrolysis result in the formation of the same non-toxic inactivation products. GD exposed to hydrogen peroxide and ammonia or short chain alkyl amines which raise the pH undergoes rapid perhydrolysis and/or hydrolysis, as long as the pH remains elevated (FIG. 6). The reaction product is largely pinacolyl methylphosphonic acid (PMPA). Exposure to hydrogen peroxide vapor alone does not cause the perhydrolysis to occur. However, when the ammonia is added to the hydrogen peroxide vapor, hydrolysis to form the non-toxic inactivation products occur. Since G-agents are hygroscopic, the ammonia tends to be readily absorbed in the moisture retained by the G-agent from the hydrogen peroxide vapor. The hydrolysis reaction results from the basicity of the ammonia and the presence of water that is absorbed in the hygroscopic GD liquid.

It will be appreciated that other chemical warfare agents which are susceptible to oxidation and/or perhydrolysis are also destroyed in the hydrogen peroxide vapor/ammonia treatment, including, but not limited to, cyanogen chloride, hydrogen cyanide, 3-quinuclidinyl benzilate (Agent BZ).

While particular reference is made to the destruction of chemical warfare agents, the method is also suited to the destruction of biological agents, such as bacterial spores, vegetative bacteria, viruses, molds, and fungi capable of killing or causing severe injury to mammals, particularly humans. Included among these are viruses, such as equine encephalomyelitis and smallpox; bacteria, such as those which cause plague (*Yersina pestis*), anthrax (*Bacillus anthracis*), and tularemia (*Francisella tularensis*); and fungi, such as coccidioidomycosis; as well as toxic products expressed by such microorganisms; for example, the botulism toxin expressed by the common *Clostridium botulinium* bacterium.

It has been found that a broad spectrum of biological and chemical agents can be deactivated (i.e., reduced to less than 1% of their original concentration by weight and preferably, reduced to undetectable levels) using the vapor hydrogen peroxide and ammonia mixture in a relatively short period of time, preferably within ten hours, and, more preferably, within about six hours. Some chemical agents, such as HD, can be deactivated in shorter time periods, e.g., from 2-6 hours. The concentration of pathogenic intermediates, e.g., VX-pyro, is preferably reduced to less than about 5% of the original weight of the chemical agent within about 24 hours.

Without intending to limit the scope of the invention, the following examples demonstrate the effectiveness of the combination of hydrogen peroxide and ammonia in deactivating chemical warfare agents.

EXAMPLES

Chemical agents VX, GD, and HD are deposited separately on glass filter papers (5 μL of the agent). The sample is placed in a 0.15 m$^3$ chamber 10 which is connected with a STERIS M-100 VHP® vaporizer. The vaporizer generates hydrogen peroxide from a solution comprising 35% hydrogen peroxide in water. Air from the chamber is used as a carrier gas. A flow rate of about 0.3 m$^3$/minute is employed. Hydrogen peroxide is injected into the carrier gas at a rate of from 0.4-0.5 g/minute, resulting in a measured hydrogen peroxide concentration within the chamber of about 600 ppm. Ammonia gas is introduced into the hydrogen peroxide and carrier gas stream just prior to its entering the chamber, at a concentration of 0.18 mL/min, resulting in a calculated ammonia concentration of about 8 ppm. The sample is exposed to the hydrogen peroxide vapor and ammonia in the chamber for a selected period of time of from about 0.5 to about 4 hours at a temperature of from about 23° C. to about 25° C.

The exposed samples and also unexposed samples are solvent-extracted and the extract analyzed for residual agent and reaction products by NMR.

Similar experiments were carried out as described above, but without ammonia.

Figure 7:
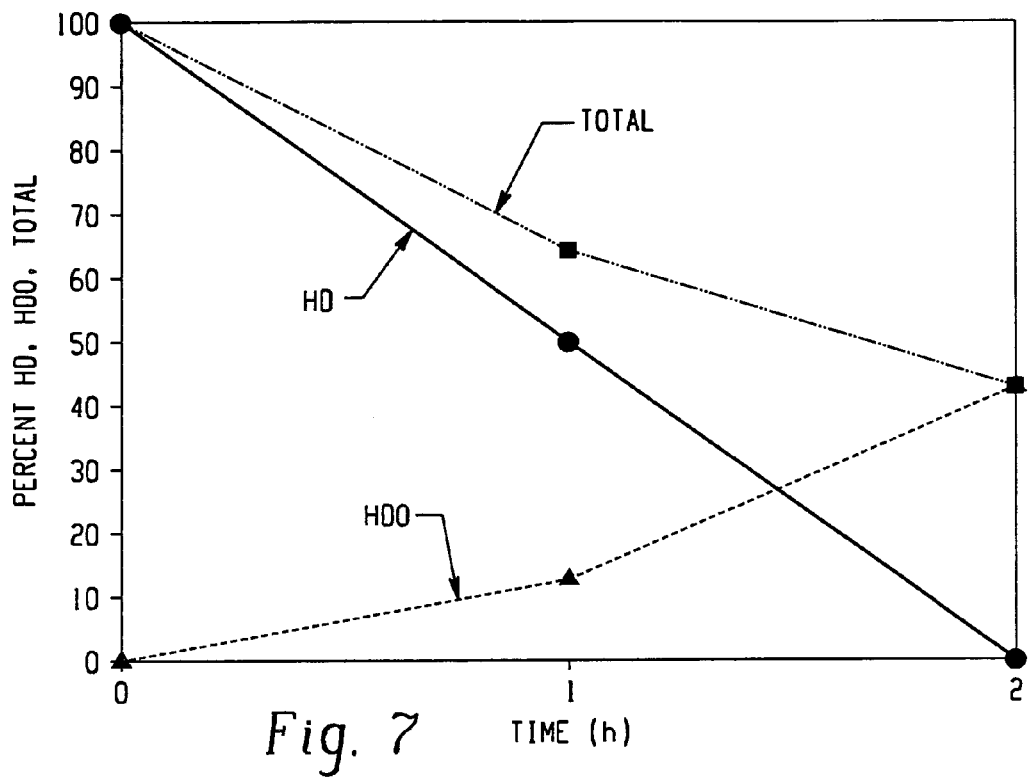
FIG. 7 is a plot of percent HD and HDO vs. time in the presence of hydrogen peroxide vapor and ammonia.

FIG. 7 is a plot of the percentage, by weight, of the initial HD detected, and the percentage of reaction product HDO (expressed as a percentage of the initial HD), vs time, in the presence of both hydrogen peroxide and ammonia. It can be seen that the HD is no longer detectable after a period of two hours. A significant portion (about 45%) is converted to HDO.

Figure 8:
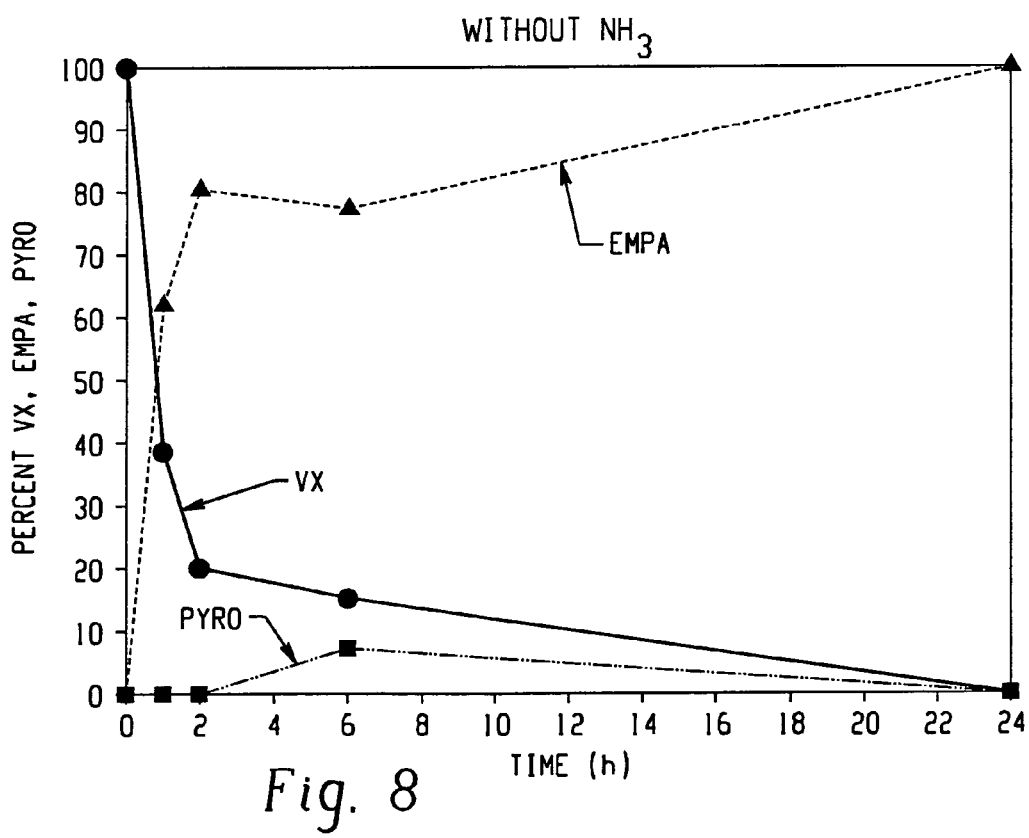
FIG. 8 is a plot of percent VX, VX-Pyro, and EMPA vs. time in the presence of hydrogen peroxide vapor without ammonia.

FIG. 8 shows the results for VX in the presence of hydrogen peroxide without ammonia, as well as those for reaction products VX-pyro and EMPA. Although the initial drop in VX is relatively fast, it takes approximately 24 hours for the VX levels to drop completely. At this time, the product is EMPA. VX-Pyro is detected as an intermediate product, which reaches a concentration peak at about six hours and then declines.

Figure 9:
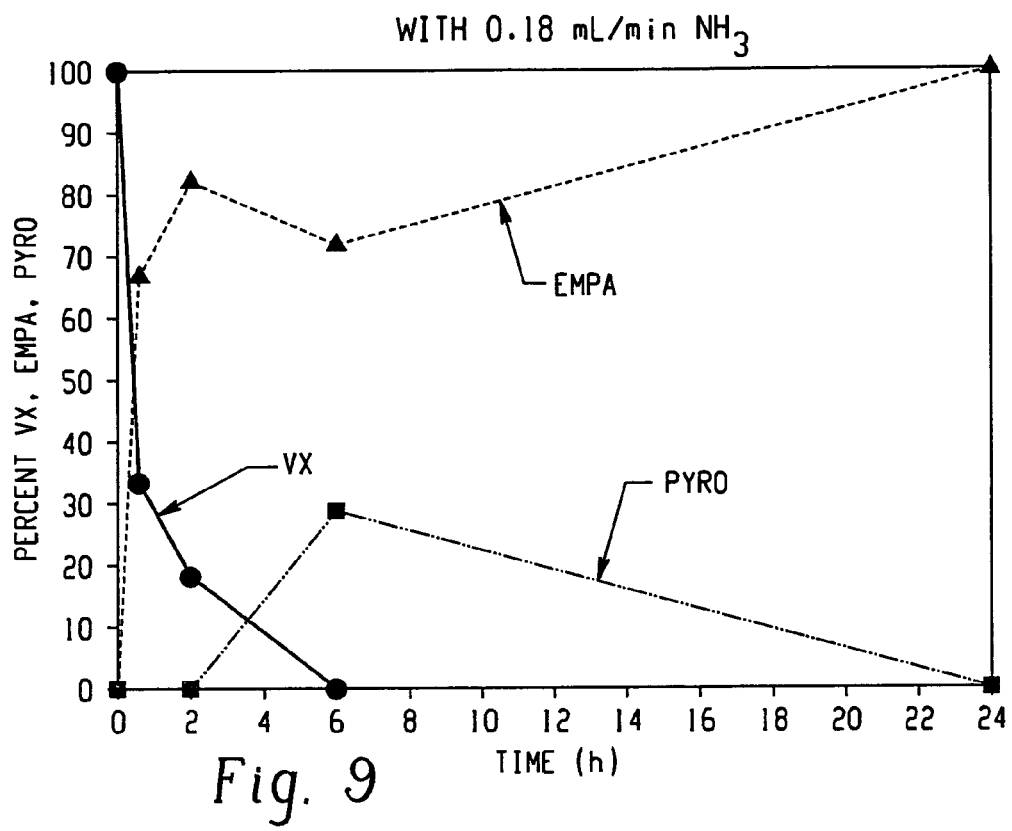
FIG. 9 is a plot of percent VX, VX-Pyro, and EMPA vs. time in the presence of hydrogen peroxide vapor with ammonia.

FIG. 9 shows the comparable results for VX in the presence of both hydrogen peroxide and ammonia. Here, the rate of decomposition of VX is much faster than without ammonia, dropping to undetectable levels within about 6 hours. After 24 hours, the reaction products are all in the form of EMPA.

Figure 10:
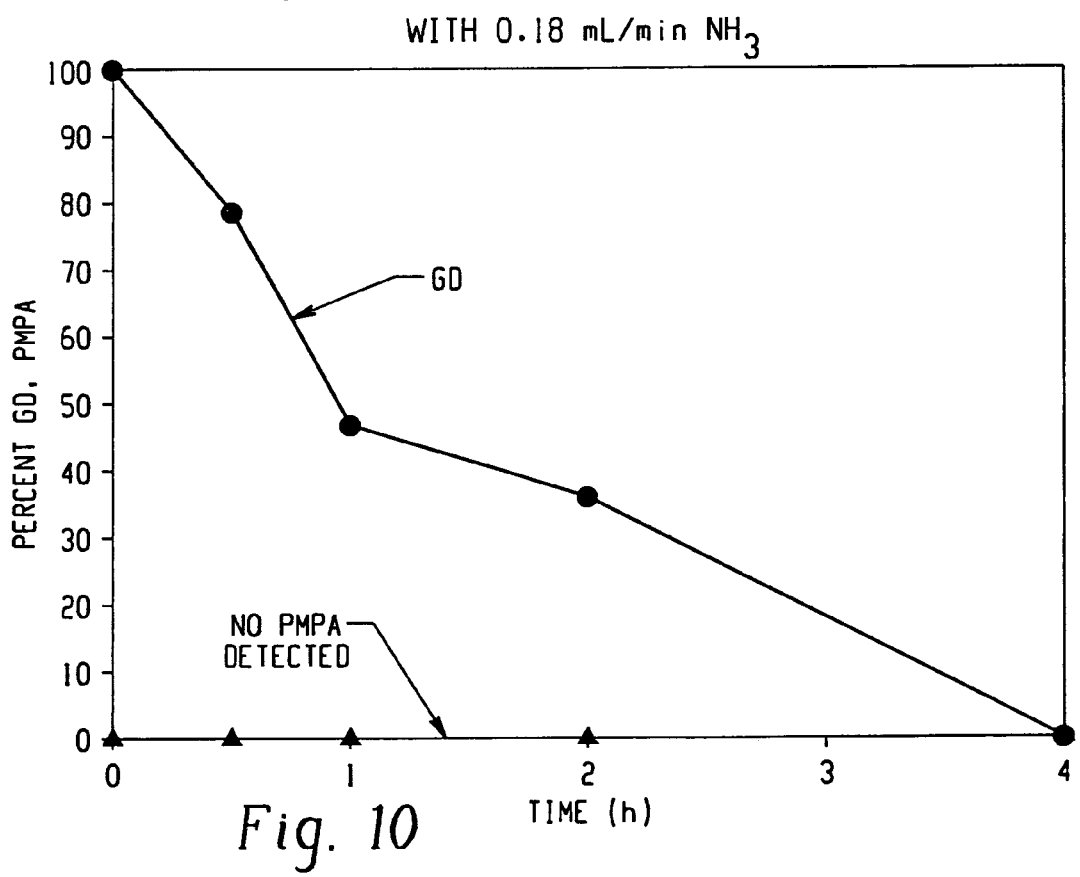
FIG. 10 is a plot of percent GD and PMPA vs. time in the presence of hydrogen peroxide vapor with ammonia.

FIG. 10 shows the results for GD in the presence of hydrogen peroxide and ammonia. The concentration of GD drops to undetectable levels within about 4 hours. No PPMA is detected. This may be due to evaporation of the reaction product from the sample.

Figure 11:
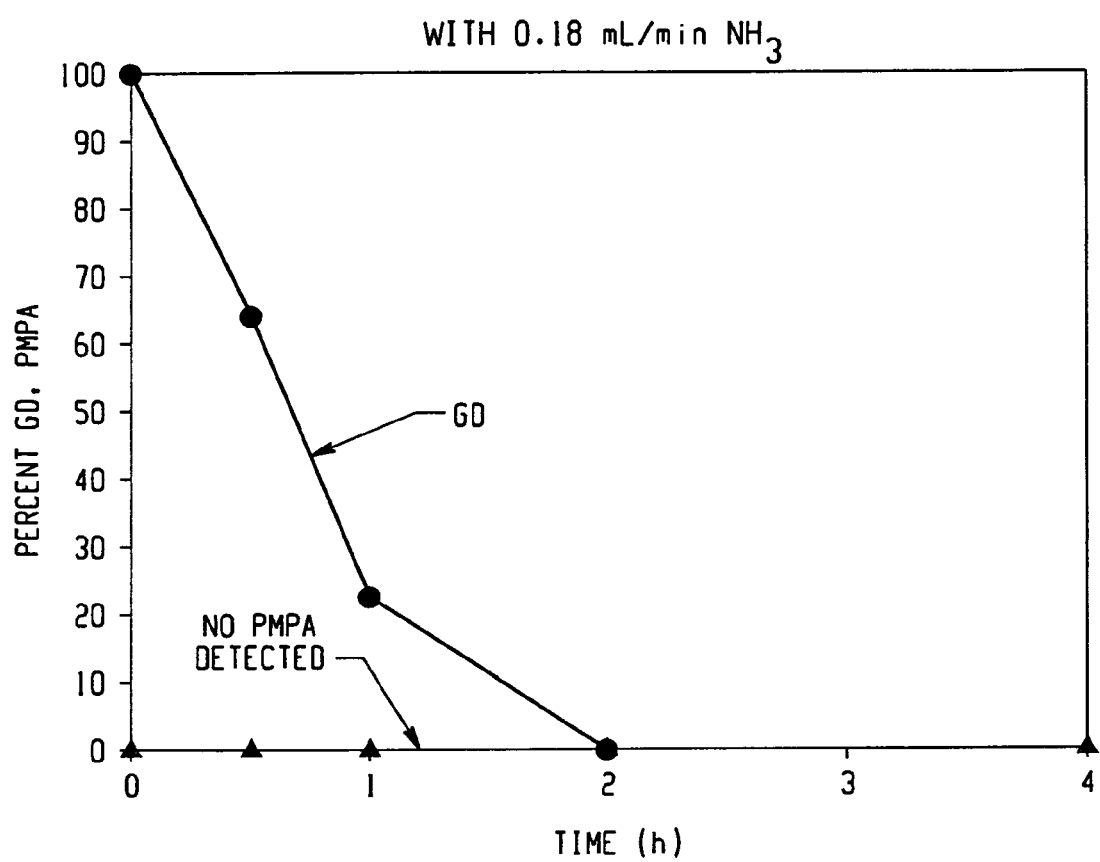
FIG. 11 is a plot of percent GD and PMPA vs. time in the presence of hydrogen peroxide vapor with ammonia under controlled water conditions.

FIG. 11 shows comparable results for GD in the presence of ammonia and water vapor as a control.

Having thus described the preferred embodiment, the invention is now claimed to be:

1. A method of deactivating a pathogenic chemical agent comprising:
   subjecting the pathogenic chemical agent to a peroxide in the form of a vapor in the presence of a nitrogen containing compound in the form of a gas, a ratio of the peroxide to the nitrogen containing compound being between 1:1 and 1:0.0001, the nitrogen containing compound being of the general formula:

$$R_1 - N - R_2$$
$$|$$
$$R_3$$

where $R_1$, $R_2$, and $R_3$ independently are selected from H and an alkyl group.

2. The method as set forth in claim 1, wherein:
the peroxide includes hydrogen peroxide.

3. The method as set forth in claim 1, wherein:
the peroxide is in the form of a vapor.

4. The method as set forth in claim 3, further including:
vaporizing a liquid peroxide compound to form a peroxide vapor.

5. The method as set forth in claim 1, wherein:
the nitrogen containing compound includes ammonia.

6. The method as set forth in claim 1, wherein:
the nitrogen containing compound includes an alkyl amine.

7. The method as set forth in claim 1, wherein:
the ammonia gas and the hydrogen peroxide vapor is present in a ratio of between 1:1 and 0.0001:1.0.

8. The method as set forth in claim 1, wherein:
the nitrogen containing compound and peroxide is in the form of a gaseous mixture.

9. The method as set forth in claim 8, wherein:
the nitrogen containing compound is at a concentration of at least 1 ppm in the gaseous mixture.

10. The method as set forth in claim 9, wherein:
the nitrogen containing compound concentration is less than about 100 ppm.

11. The method as set forth in claim 10, wherein:
the nitrogen containing compound concentration is at least about 3 ppm in the gaseous mixture and less than about 20 ppm.

12. The method as set forth in claim 11, wherein:
the nitrogen containing compound includes ammonia at a concentration of about 8 ppm.

13. The method as set forth in claim 8, wherein:
the peroxide is at a concentration of at least 50 ppm in the gaseous mixture.

14. The method as set forth in claim 8, wherein:
the peroxide is at a concentration of less than 1000 ppm in the gaseous mixture.

15. The method as set forth in claim 14, wherein:
the peroxide is at a concentration of at least 400-800 ppm in the gaseous mixture.

16. The method as set forth in claim 15, wherein:
the nitrogen containing compound includes ammonia at a concentration of from about 3-20 ppm.

17. The method as set forth in claim 16, wherein:
the temperature is about 23-25° C.

18. The method as set forth in claim 16, wherein:
the peroxide includes hydrogen peroxide at a concentration of about 600 ppm in the gaseous mixture.

19. The method as set forth in claim 18, wherein:
the nitrogen containing compound includes ammonia at a concentration of about 8 ppm in the gaseous mixture.

20. The method as set forth in claim 13, wherein:
the peroxide concentration is at least about 200 ppm in the gaseous mixture.

21. The method as set forth in claim 8, wherein:
the gaseous mixture further includes a carrier gas.

22. The method as set forth in claim 21, wherein:
the carrier gas includes air.

23. The method as set forth in claim 1, wherein:
the chemical agent includes at least one of G-type, V-type, and H-type chemical agents, and combinations thereof.

24. The method as set forth in claim 23, wherein the chemical agent includes a G-type chemical agent and the method further includes:
contacting the pathogenic chemical agent with the nitrogen containing compound and peroxide for sufficient time to reduce the G-type agent to a level of less than 1% of its original concentration.

25. The method as set forth in claim 24, wherein:
the contacting time is up to about six hours.

26. The method as set forth in claim 1, further including:
maintaining the temperature during the step of subjecting at from about 15° C. to about 30° C.

27. The method as set forth in claim 1, wherein the nitrogen containing compound is a liquid and the method further includes:
vaporizing the liquid in a vaporizer.

28. A method for decontamination of an item contaminated with GD, the method comprising:
contacting the item contaminated with GD in an enclosure with a vapor containing a peroxide and ammonia for sufficient time to reduce the concentration of GD to less than about 1% of its initial concentration, the time for the concentration to reach 1% of its initial concentration being less than 6 hrs.

29. A method of deactivating a pathogenic chemical agent comprising:
forming a peroxide vapor;
increasing the pH of the vapor with a pH-increasing compound;
subjecting the pathogenic chemical agent to the peroxide at the increased pH to deactivate the chemical agent, thereby reducing the concentration of the chemical agent to less than 1% of the original concentration by weight.

30. The method as set forth in claim 29, wherein the peroxide includes hydrogen peroxide and the pH-increasing compound includes ammonia.

31. A method of deactivating a pathogenic chemical agent comprising:
forming a peroxide vapor comprising hydrogen peroxide;
increasing the pH of the vapor with a pH-increasing compound comprising ammonia, wherein the hydrogen peroxide is at a concentration of from about 200-800 ppm and the ammonia is at a concentration of from 3-40 ppm; and
subjecting the pathogenic chemical agent to the peroxide at the increased pH to deactivate the chemical agent, thereby reducing the concentration of the chemical agent to less than 1% of the original concentration by weight.

32. The method as set forth in claim 31, wherein the temperature is room temperature.

33. A method of deactivating a biologically active substance comprising:
subjecting the biologically active substance to a mixture of a strong oxidant compound and an alkaline compound, both in a gaseous form, the alkaline compound in gaseous form includes a mist formed by atomizing a liquid alkaline compound.

34. The method as set forth in claim 33, wherein:
the strong oxidant includes a peroxy compound.

35. The method as set forth in claim 34, further including:
vaporizing a liquid peroxy compound to form a peroxy vapor.

36. The method as set forth in claim 33, wherein:
the alkaline compound includes a short chain alkyl amine.

37. The method as set forth in claim 33, wherein:
the peroxy compound includes hydrogen peroxide.

38. The method as set forth in claim 33, wherein:
the biologically active substance includes one or more of chemical agents, pathogens, prions, and biotoxins.

39. The method as set forth in claim 38, wherein:
the biologically active substance includes G-type nerve agents.

40. The method as set forth in claim 28, wherein:
the ammonia gas and the hydrogen peroxide vapor are present in a ratio of between 1:1 and 0.0001:1.0.

* * * * *